United States Patent [19]

Leas

[11] 4,274,839
[45] Jun. 23, 1981

[54] PROCESS FOR GASIFICATION OF COAL AND ORGANIC SOLID WASTES

[76] Inventor: Arnold M. Leas, 122 N. 34th St. Towne House Village, Richmond, Ind. 47374

[21] Appl. No.: 108,110

[22] Filed: Dec. 28, 1979

[51] Int. Cl.³ .............................................. C10J 3/54
[52] U.S. Cl. ................................... 48/202; 48/197 A; 48/209; 55/71; 252/373; 423/230; 423/240; 423/657
[58] Field of Search ................... 48/197 R, 262, 203, 48/206, 209, 197 A, 200, 201; 252/373; 423/658, 230, 240, 657; 55/71

[56] References Cited

U.S. PATENT DOCUMENTS

| | | | |
|---|---|---|---|
| 2,276,343 | 3/1942 | Reyerson et al. | 48/202 |
| 2,579,397 | 12/1951 | Roetheli | 48/206 |
| 2,614,038 | 10/1952 | Barr | 48/206 |
| 3,031,287 | 4/1962 | Benson et al. | 48/197 R |
| 3,222,147 | 12/1965 | Benson | 48/197 R |
| 3,750,372 | 8/1973 | Cyr et al. | 55/71 |
| 3,900,298 | 8/1975 | Cyr et al. | 55/71 |
| 3,966,634 | 6/1976 | Sacks | 48/197 R |
| 3,977,844 | 8/1976 | Van Slyke | 48/209 |
| 4,152,119 | 5/1979 | Schulz | 252/373 |
| 4,206,186 | 6/1980 | Holter et al. | 423/230 |

FOREIGN PATENT DOCUMENTS

2189101 3/1974 France ........................................ 55/71

Primary Examiner—Peter F. Kratz
Attorney, Agent, or Firm—Baker & McKenzie

[57] ABSTRACT

Disclosed is a process for coal and organic solid waste gasification using a granular fluidized bed of clay to produce hydrogen and carbon monoxide. The clay used in the gasification is circulated to an air burner to obtain producer gas via burning of carbon deposited thereon and then recirculated to the gasifier. The producer gas is used to reduce a metal oxide and the reduced metal is reoxidized with steam to generate hydrogen gas.

10 Claims, 10 Drawing Figures

PROCESS FOR GASIFICATION OF COAL AND ORGANIC SOLID WASTES

TECHNICAL FIELD

This invention relates to the conversion of multi-solid, non-petroleum fuels (such as municipal, agricultural, and industrial solid wastes, coal, shale oil, and tar sands) into clean liquid and/or gaseous fuels.

BACKGROUND OF THE INVENTION

The primary reason that clean fluid fuel production other than from petroleum and natural gas has not been commercialized to date is that an economical process has not been developed to convert more abundant and less costly multi-solid fuels into clean fluid fuels. However, an integrated process for converting multi-solid fuels economically into clean gaseous and liquid fuels is described herein.

In the prior art, high capital and operating costs have not justified the commercialization of municipal, industrial, and agricultural solid waste conversion to clean liquid and gaseous fuels. The maintenance costs in shredding and/or hammer-milling the contained inorganics have been excessive relative to the value of the raw solid waste feed stocks. The environmental problems posed by such conversion have been complex and intractable. Finally, with specific reference to prior art coal conversion processes, the cost of the necessary treating reagent solid wastes disposal system have been intolerable.

Moreover, mere disposal of such solid wastes has become a problem. Atmospheric incineration has been very inefficient because of the high water content of the solid wastes and because of excessive toxic emissions unless costly scrubbers have been used. Land filling of solid wastes has become increasingly less feasible in many areas because the leaking of water pollutants could become a serious problem to future generations.

OBJECTS OF THE INVENTION

It is, therefor, an object of the present invention to overcome the inadequacies and serious economic and environmental problems of the prior art processes for converting multi-solid fuels to clean fluid fuels and valuable by-products, including electricity.

It is a further object of the present invention to composite and sequence the operation of the conversion process to recover virtually all the processing energy and to upgrade the non-energy by-products of the process so that the overall economics are attractive.

It is a still further object of the present invention to process various solid feed stocks and to produce various products to accommodate changing demands over time.

It is another object of the present invention to recover and use the residual heat and condensed steam from the process exhaust gases as recyclable hot water to gravity separate the solid wastes, regenerate the treating reagents, dissolve and selectively re-precipitate the valuable metal by-products, and to disintegrate the organic combustible portion of the feed stock to facilitate mud pumping the organic combustible portion of the feed stock into the coal reactor gasifier.

It is yet another object of the present invention to use barium carbonate to remove residual chlorine gases from the coal reactor and then regenerate and recycle the barium as a continuous treating agent.

It is yet another object of the present invention to use limestone ($CaCO_3$) to remove hydrogen sulfide from the coal reactor as calcium sulfide and calcium sulfate, to externally air oxidize the calcium-sulfide to calcium sulfate, and to use a portion of the calcium sulfate in the hot water circulating system to produce ammonium sulfate while concurrently regenerating and recycling the calcium carbonate to the coal reactor.

Yet another object of the present invention is to separate polyvinyl chloride plastics from polyethylene plastics in the hot water separation, in which the polyvinyl chloride plastics (which have a specific gravity of 1.5) sink and the polyethylene plastics (which have a specific gravity of 0.9) float, to separate the corrosive polyvinyl chloride plastics from the feed stock, and to thereby prevent them from being pumped into the coal reactor.

Another object of the present invention is to use barium carbonate as a high temperature precipitating agent at the top contact tray of the coal reactor to remove fine particulates and vaporous metal chlorides or fluorides.

A further object of the present invention is to circulate clay from the coal reactor bottom gasifying zone to supply process heat and to air-burn the carbon externally to its oxides ($CO$ and $CO_2$) to provide a dry gas for reducing metals, for drying coal, etc.

A further object of the present invention is to generate hydrogen by contacting steam to the circulating reduced metal reagent (stainless steel powders).

Yet another object of the present invention is to circulate hot ash through solid-water slurries to generate low cost process steam.

Yet another objet of the present invention is to use large quantities of excess process air to oxidize calcium sulfide to calcium sulfate and to pre-heat the air.

Yet a further object of the present invention is to consolidate the foregoing operations to minimize capital and operating costs of the composite plant.

Other objects and advantages of the present invention will become apparent from the following detailed description of a preferred embodiment thereof taken in conjunction with the accompanying drawings.

BRIEF SUMMARY OF THE INVENTION

A brief description of each compartmental unit and how the operation of each is integrated into the total process is set forth below.

A. Solid Waste Hot Water Gravity Separating Unit

The primary source of the water makeup is the sewage water in municipal wastes and/or the waste water in agricultural and industrial wastes. Additional water makeup comes from water contained in the solid fuel charging stocks and by condensation of the excess recycle steam in the exhaust gases from the process plant.

The primary source of heat comes from exhaust gases and from the condensation of steam in the exhaust gases.

The solid waste feed stocks originate from municipal, industrial, and agricultural sources and therefore vary over time in quality and quantity. The sewage water solid concentrates originate from municipal and industrial areas.

The intermediate products conveyed from the coal reactor to the water separating unit include calcium sulfate, ammonia, barium chloride, ash, exhaust gases, and steam. The products conveyed from the water separating unit to the coal gasifier unit include calcium carbonate and barium carbonate for treating, organic solid waste mud slurry, steam condensate, and some recycled carbon dioxide pressurizing gas. Some of the by-products conveyed to storage from the gravity separating unit are ammonium sulfate fertilizer, iron hydroxide, aluminium hydroxide, cooled exhaust gases, sodium chloride, inorganic solid wastes such as glass and dirt, polyvinyl chloride plastics, some water vapor, and some coal ash.

In operation, chopped municipal solid wastes and recovered industrial solid wastes are conveyed into the exhaust stack, and chopped agricultural solid wastes are pumped as a water slurry into the exhaust stack. The slightly acidic water in the exhaust stack dissolves the iron and aluminum cans from the municipal solid waste fraction, creating iron and aluminum sulfates, and a portion of the circulating water is diverted and concentrated by water evaporation to ammonia precipitate the iron and aluminum to hydroxides to yield a valuable chemical by-product. After the iron and aluminum hydroxide slurry is removed, the decanted clear water is contacted with carbon dioxide to precipitate calcium and barium carbonate, which are treating agents. The regenerated treating reagents are then dried and recycled back to the coal reactor to remove the sulfur and chlorine gases. The final clear water is further concentrated to yield ammonium sulfate fertilizer and other valuable chemical by-products. Depending on the feedstock, various herbicides and fungicides, as well as potash and phosphate are recovered and included with the ammonium sulfate fertilizer water slurry. For some end users some of the coal ash powder is also included as a soil conditioner in the fertilizer water slurry. Because chlorine is a processing trouble maker, the barium chloride is removed by treating the slurry with water and sodium carbonate to remove the chlorine as sodium chloride (salt water). The barium carbonate is then dried and recycled as a treating reagent.

The organic solid wastes float on top of the hot water and flow into a mechanical grinder. A substantial portion of the water is evaporated, and the concentrated organic solid wastes are then mud pumped to a pressure steam generator and then pressured into the coal reactor. A vacuum pump pulls the carbon dioxide out of the water and recycles it to the processing unit.

The balance of the gravity separating unit is quite conventional to those familiar with this art.

B. Coal Feed System

Pulverized coal gravitates from a coal hopper to two or more lock-bins. Several different pressurizing agents may be used to lock-bin the coal into the coal reactor. An auger system with a variable speed motor is a good method to precisely control the coal feed input.

C. Coal Reactor

The steam and recycled carbon dioxide gasify the organic solids and coal feed to primarily carbon monoxide and hydrogen ($H_2O + C + CO_2 \rightarrow CO + H_2$). Circulating hot clay (i.e., clay with carbon deposited thereon) and the external air burner provides nearly all the process heat for the entire plant. Red hot (1700° F.) fluidized clay within the coal reactor drives ash powder (which is of lower density) up through a first chimney into a lower velocity area, where 98% of the ash powder is settled into an annular ash accumulator. A small amount of steam removes a substantial portion of the carbon from the ash. The ash is then pressured through a cooler, in which its temperature is lowered from 1500° F. to 1000° F., and into the air burner. In the air burner the residual carbon is removed, and the ash is fractionated into coarse and fine powders. The fine hot ash is then pressured into a first disengager tower and from there to both the organic solids steam generator and a pre-water evaporator. The coarse hot ash is pressured into a second disengager tower, and from there it is split into three streams. The first stream goes to an ammonium sulfate concentrator, the second stream goes to a recycle limestone drier, and the balance goes to product storage.

Clay at 1000° F. is circulated from the bottom of the coal reactor to a surge tank as a dense phase and then to and through a pipe riser reactor in a dilute phase to a clay separating tower. Air burns the carbon off the clay to yield carbon monoxide and some carbon dioxide. Within the clay separating tower the clay is concentrated, and dense clay is then recycled on level control to the bottom of the coal reactor. Hot producer gases are pressured through a treating reactor, into a chemical combustor tower, then into gas expanders and exchangers, and finally into exhaust heat recovery stacks leading to the atmosphere.

A circulating metal reagent is reduced in the chemical combustor tower, and steam oxidizes the metal reagent to produce hydrogen as the oxidized metal reagent powder circulates to an elevated chamber in each disengager. In the disengagers the hydrogen is discharged overhead and the oxidized metal is recycled out the bottom to the chemical combustor tower. When nitrogen is required for ammonia production, some air is injected into the disengagers to add more oxygen to the metal reagent prior to its descent to the chemical combustor tower.

As the hot producer gas moves upward in the coal reactor, hydrogen sulfide is converted to calcium sulfide in a lime treater section, and hydrogen chloride is converted to barium chloride. Because the barium chloride has the higher density, it is withdrawn at this level as a separate product and regenerated as previously discussed. The calcium sulfide has a lower density, and it is therefore removed in the next upper product draw tray and then processed as discussed above. The residual micronic particulates and vaporized metallic chlorides are then removed by a high temperature precipitator in the top contact tray, leaving a very clean producer gas product consisting primarily of hydrogen and carbon monoxide. The hydrogen and carbon monoxide are then used to produce methyl alcohol in a conventional process unit, and the vent gases from the methyl alcohol unit are recycled back into the coal reactor to provide the right ratio of hydrogen and carbon monoxide to maximize alcohol production.

D. Calcium Sulfide Oxidizer

The process air flows through a calcium sulfide oxidizer to convert the calcium sulfide to calcium sulfate. The calcium sulfate then becomes a product a portion of which is recycled back to the gravity separating unit as discussed above. The excess air from the calcium sulfide oxidizer is preheated substantially to improve the efficiency of the clay separating tower, in which it is used to burn the carbon off the circulating clay.

E. Electrical Production

Nitrogen and carbon dioxide from the chemical combustor tower are used to drive an air compressor and a gas expander, which in turns powers an electrical generator.

F. Water Makeup Treaters

Since the steam condensate is recycled, the water treating reagent requirements are quite low.

G. Inventory Control

The total process plant is designed to operate at coal reactor design capacity on a continuous basis except for a probable yearly inspection and/or maintenance period. Since municipal solid wastes tend to degrade in storage, the preferred shutdown period would be in the colder months. The larger amounts of agricultural wastes produced during harvest periods could be compensated for by proportional reductions in the coal feed. Industrial solid wastes could be scheduled as needed. In the event the dried, powdered solid wastes need to be put in intermediate storage, they could later be recharged in with the pulverized coal feed. Product storage would have to be provided to accommodate the consumers of each product.

BRIEF DESCRIPTION OF THE DRAWINGS

FIG. 5A through 5F are portions of a single large schematic drawing of the subject invention. These pages may be lined up with FIGS. 5A through 5D adjacent each other along their lateral edges and FIGS. 5E and 5F lieing with their long sides along the bottoms of FIGS. 5A through 5D.

DETAILED DESCRIPTION OF THE PRESENTLY PREFERRED EMBODIMENT

Figure 1:
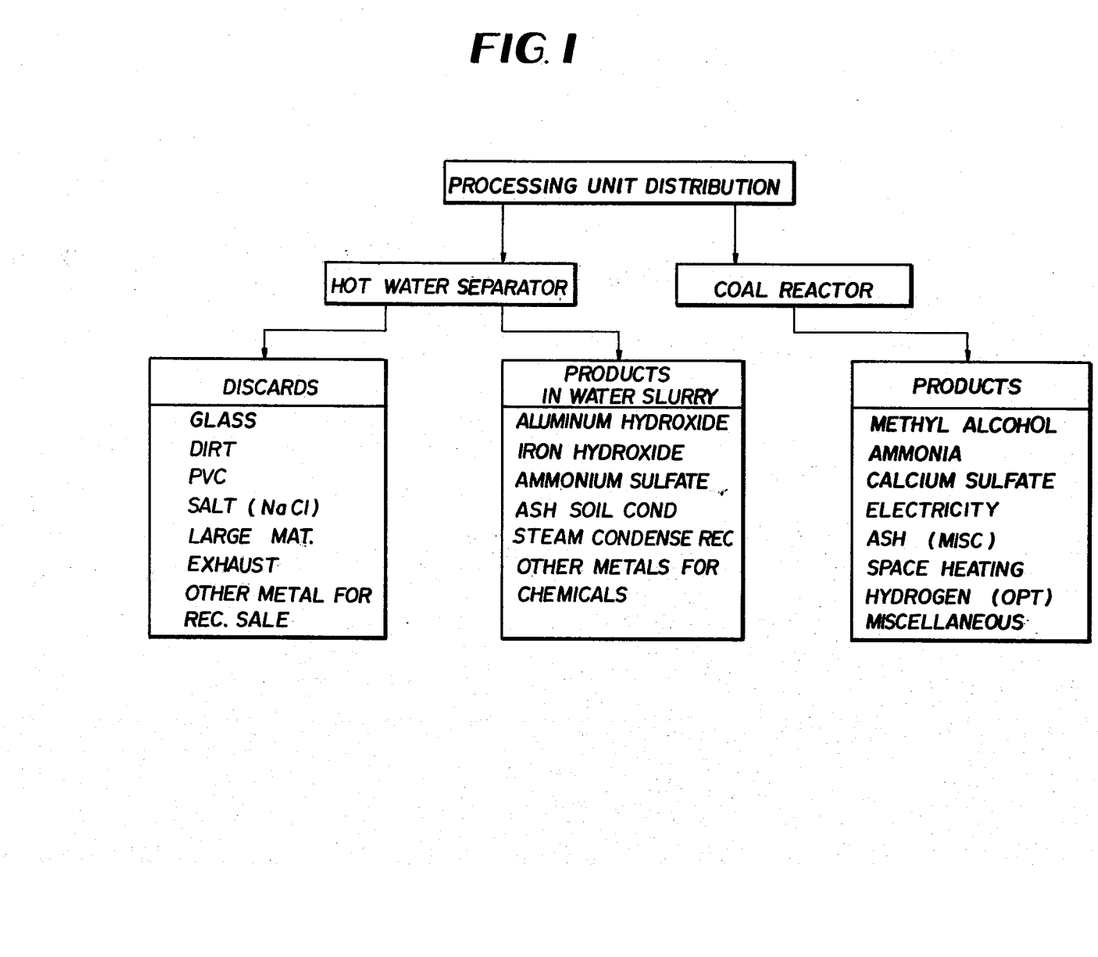
FIG. 1 is a flow chart of the subject invention in highly schematic form.

FIG. 1 is a flow chart showing the subject invention in highly schematic form. It shows the major product streams for both the hot water separator and the coal reactor, as well as the discards, which come primarily from the hot water separator.

Figure 2:
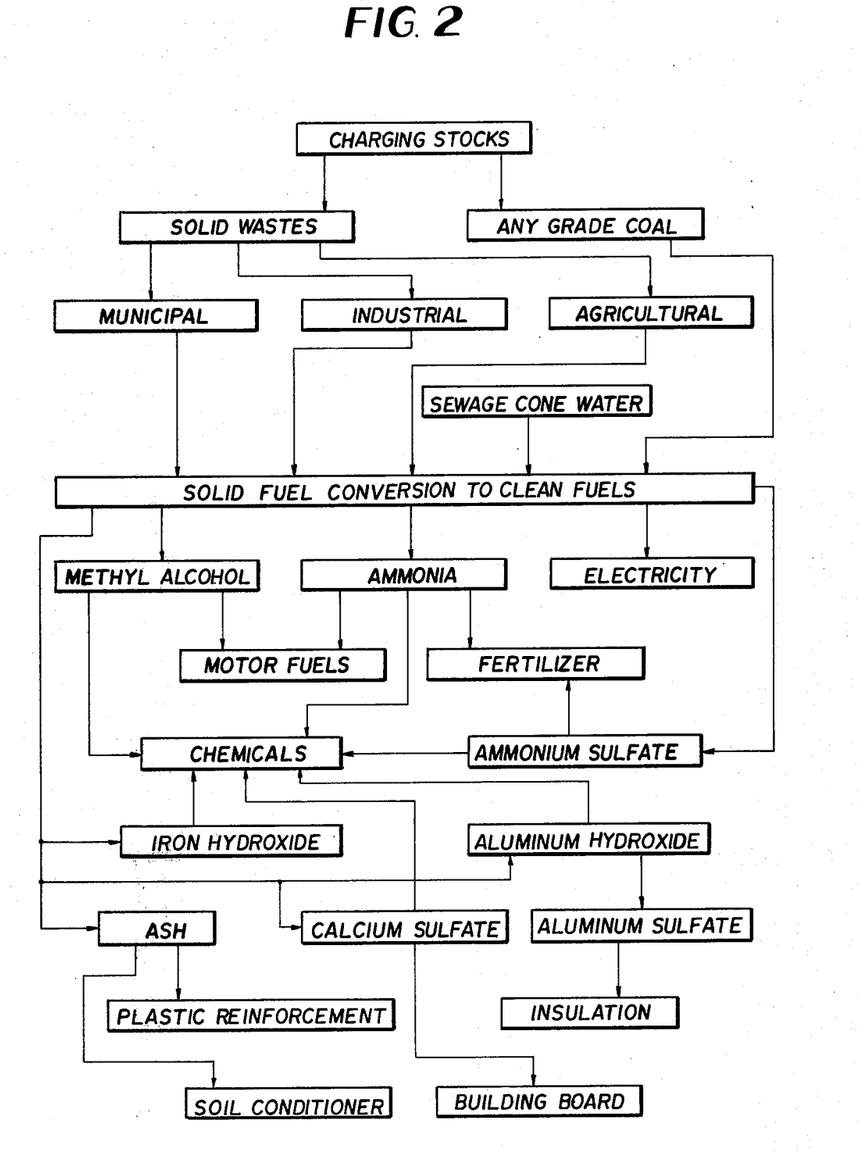
FIG. 2 is a flow chart of the subject invention in more detailed form.

FIG. 2 is also a flow chart of the subject invention. It is still in schematic form, but it shows more details than did FIG. 1. In particular, it shows various products of the process, which include such commercially valuable by-products as electricity, fertilizer, and ash as well as the clean fuels (notably methyl alcohol) which are the principal products of the process.

Simplified Form of the Invention

Figure 3:
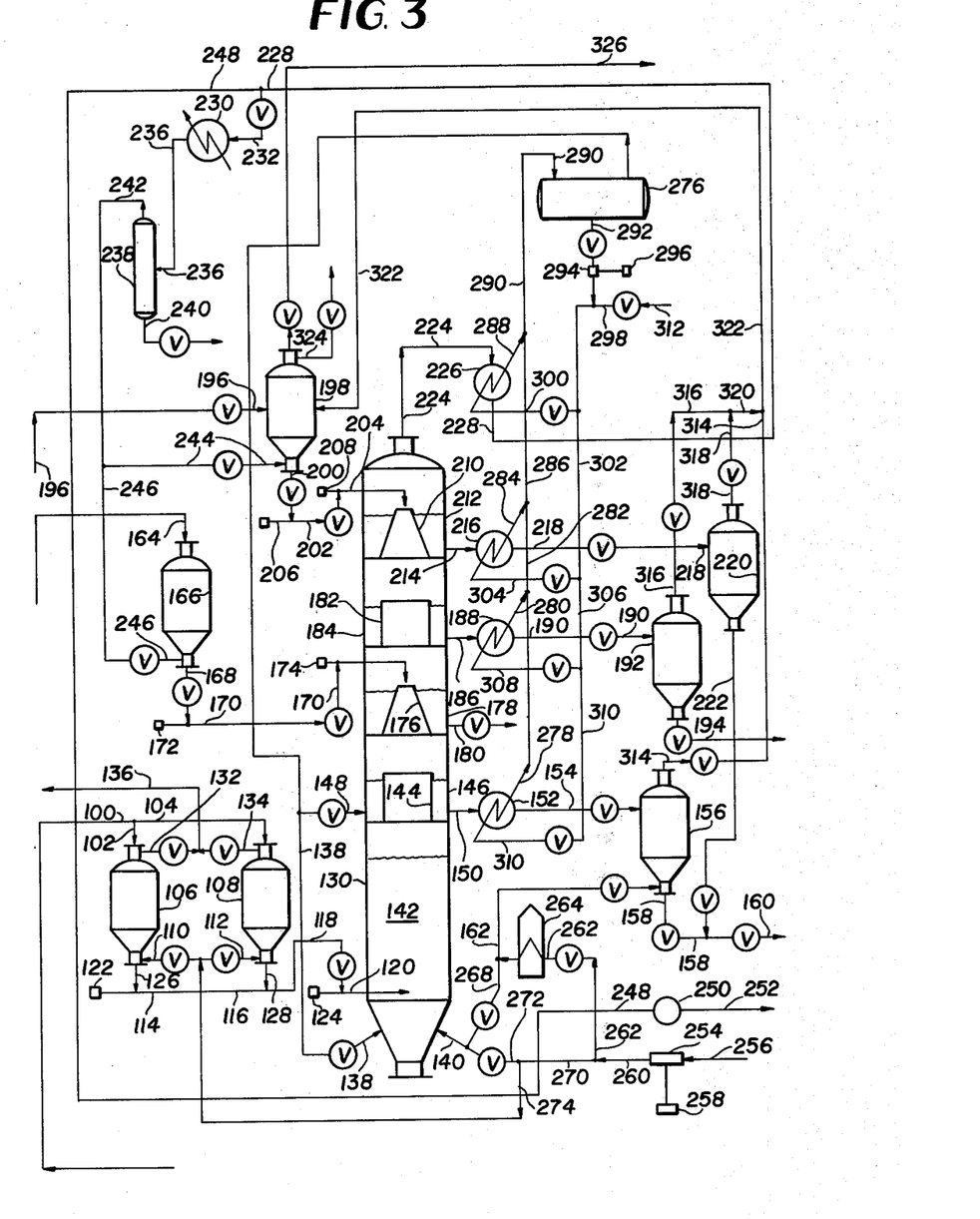
FIG. 3 is a schematic drawing of a simplified form of the subject invention.

FIG. 3 is a schematic drawing of a simplified form of the subject invention. When using the simplified form, air is used along with steam to gasify the carbonaceous feed stocks.

Combustibles, steam, and air are fed into the lowest tray, in which the gasification reactions take place. The red-hot, fixed, fluidized bed of clay is used to accelerate the gasification process and to drive the powdered ash to the next upper tray, wherein the ash is gravitated out to the annular section. The producer gas is then contacted in the next upper tray with powdered calcium and barium carbonates to remove the sulfur and chlorine gases. Because the barium chloride is more dense, it is discharged from the bottom of this treating tray. Because the calcium sulfide is less dense, it flows to the next upper tray to be accumulated and discharged from its annular area. The producer gas then is contacted with the high temperature precipitating agent in the top contact tray to remove the submicronic particulates and the metallic vapors (i.e., the iron chlorides). Thereafter, these final solid particulates are conglomerated and settled to the bottom of the top tray to then be discharged as an ash product. The final ultra-clean hot producer gases then discharge at the top of the tower via steam generation coolers. A small portion of the producer gases are further cooled and recycled to pressure in the treating reagents. The net producer gases drive the air compressor via a gas expander and then flow to the clients' appliances as a clean saleable fuel gas (CO & $H_2$). The by-products, ash and calcium sulfide, are discharged via coolers and depressuring pots, after which they are transported to their respective product sale facilities.

As shown in FIG. 3, combustibles flow via lines 100, 102, and 104 into lock-bins 106 and 108. Pressurized air from lines 110 and 112 and augers 114, 116, 118, and 120 driven by motors 122 and 124 force the feed through lines 126 and 128 and augers 114, 116, 118, and 120 into a gasifier treater reactor 130. Air vents 132 and 134 leading to exhaust line 136 are used when filling the lock-bins 106 and 108. At the very bottom of the reactor 130, steam and air are metered in through the lines 138 and 140, respectively, as the gasifying agents. A fixed bed of clay 142 provides intimate contact between the combustibles and the gasifying agents in a fluidized state. Because the powdered ash is lighter than the clay, it floats through a chimney 144 and then overflows into an annular accumulator 146. The ash is decarbonized by injecting some steam via line 148. The ash is then pressured out via line 150 and cooler 152, line 154 and ash decarbonizer 156, and then to storage via lines 158 and 160. More carbon is removed from the ash by injecting air from line 162 into the ash decarbonizer 156.

Calcium and barium carbonates from line 164, lock-bin 166, line 168 and auger 170 powered by motors 172 and 174 are injected into the reactor 130 to remove sulfur and chlorine gases via a perforated contact tray 176. The barium chlorides are removed from an accumulator 178 via line 180. The lighter calcium sulfide powder floats upward via chimney 182, overflows to annular accumulator 184, then pressures out via line 186, cooler 188, and line 190 to depressuring pot 192, and then to storage via line 194.

High temperature precipitating agent (HTP) is pressured in line 196 to lock-bin 198, and from there via line 200 and augers 202 and 204, powered by motors 206 and 208, respectively, to perforated contact tray 210. The spent HTP and conglomerated ash are discharged via accumulator 212, line 214, cooler 216, and 218, and depressurizing pot 220. The residual ash is then pressured to storage via lines 222 and 160. Clean producer gas (CO & $H_2$) is then pressured out of the top of the treater reactor 130 via line 224, cooler 226, and line 228. A small portion of the producer gas enters cooler 230 via line 232. It then passes through line 236 to compresser 238, which has an exhaust 240. From there it is pressured via lines 242 and 244 to lock-bin 198 and via lines 242 and 246 to lock-bin 166. The net producer gas is pressured via line 248, gas expander 250, and line 252 to the clients' appliances.

An air compressor 254 is supplied by intake line 256 and powered by motor 258. The air compressor 254 supplies air to the ash decarbonizer 156 via line 260, line 262, startup heater 264, and line 162. The air compressor 254 also supplies air to the treater reactor 130 via line 260, line 262, start-up heater 264, line 268, and line 140 or, alternatively, via line 260, line 270, line 272, and line 140. Additionally, the air compressor 254 supplies air to the lock-bins 106 and 108 via line 260, line 270, line 274, and lines 110 and 112, respectively.

Steam from coolers 152, 188, 216, and 226 is supplied to steam generator 276 via lines 278, 280, 282, 284, 286, 288, and 290, and cooling water is returned to the coolers 152, 188, 216, and 226 via line 292, pump 294 driven by motor 296, and lines 298, 300, 302, 304, 306, 308, and 310. Make-up water is supplied via line 312.

Exhaust from the ash decarbonizer 156 and the depressuring pots 192 and 220 is supplied to the lock-bin 198 via lines 314, 316, 318, 320 and 322. Exhaust from the lock-bin 198 may be vented via line 324 or transferred to storage via line 326.

Multi-tray Gasifier-Treater Reactor and Methanol Converter Reactor

Figure 4:
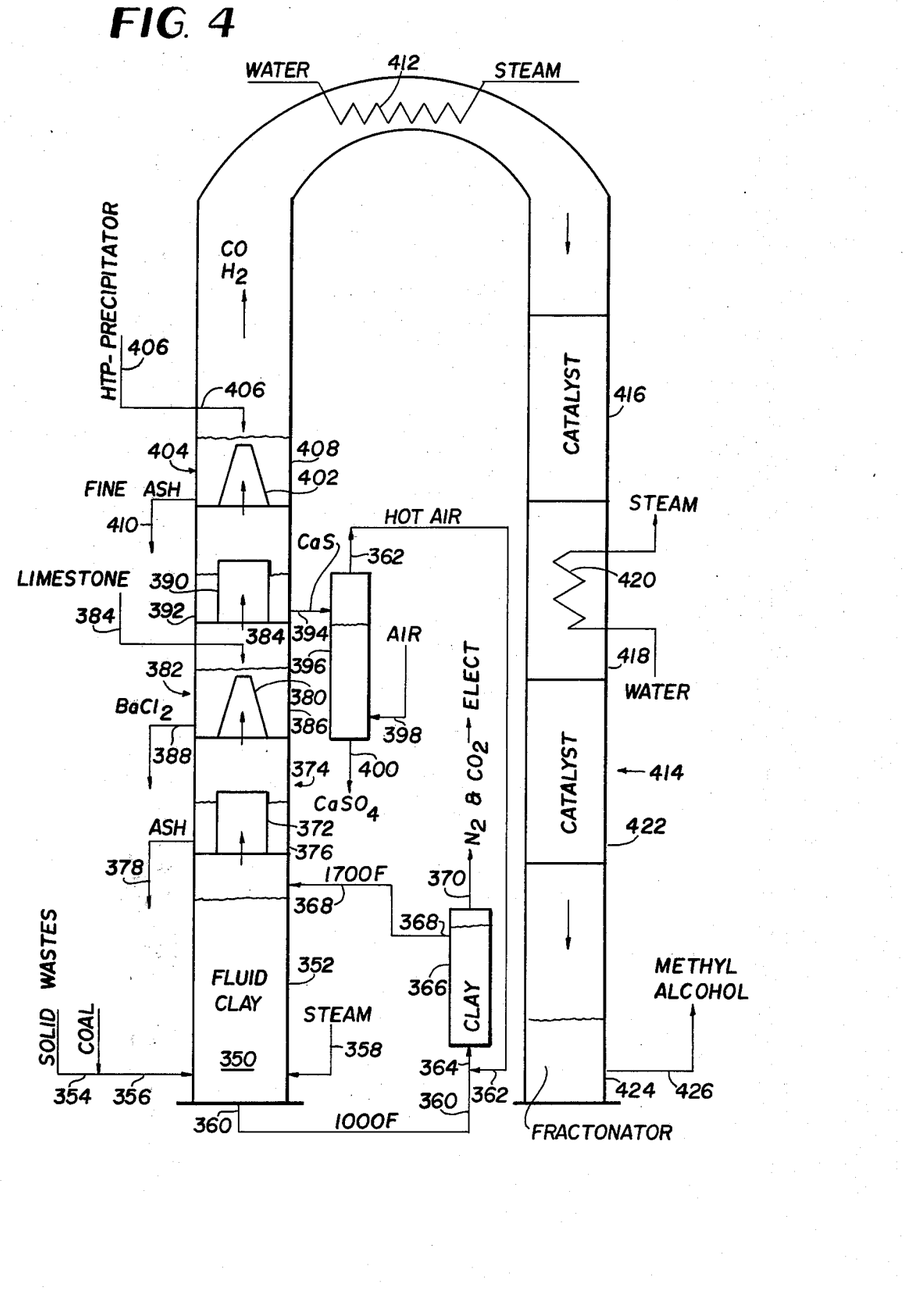
FIG. 4 is a schematic drawing of a gasifier-treater reactor and of a methanol converter reactor suitable for use with the subject invention.
Figure 5A:
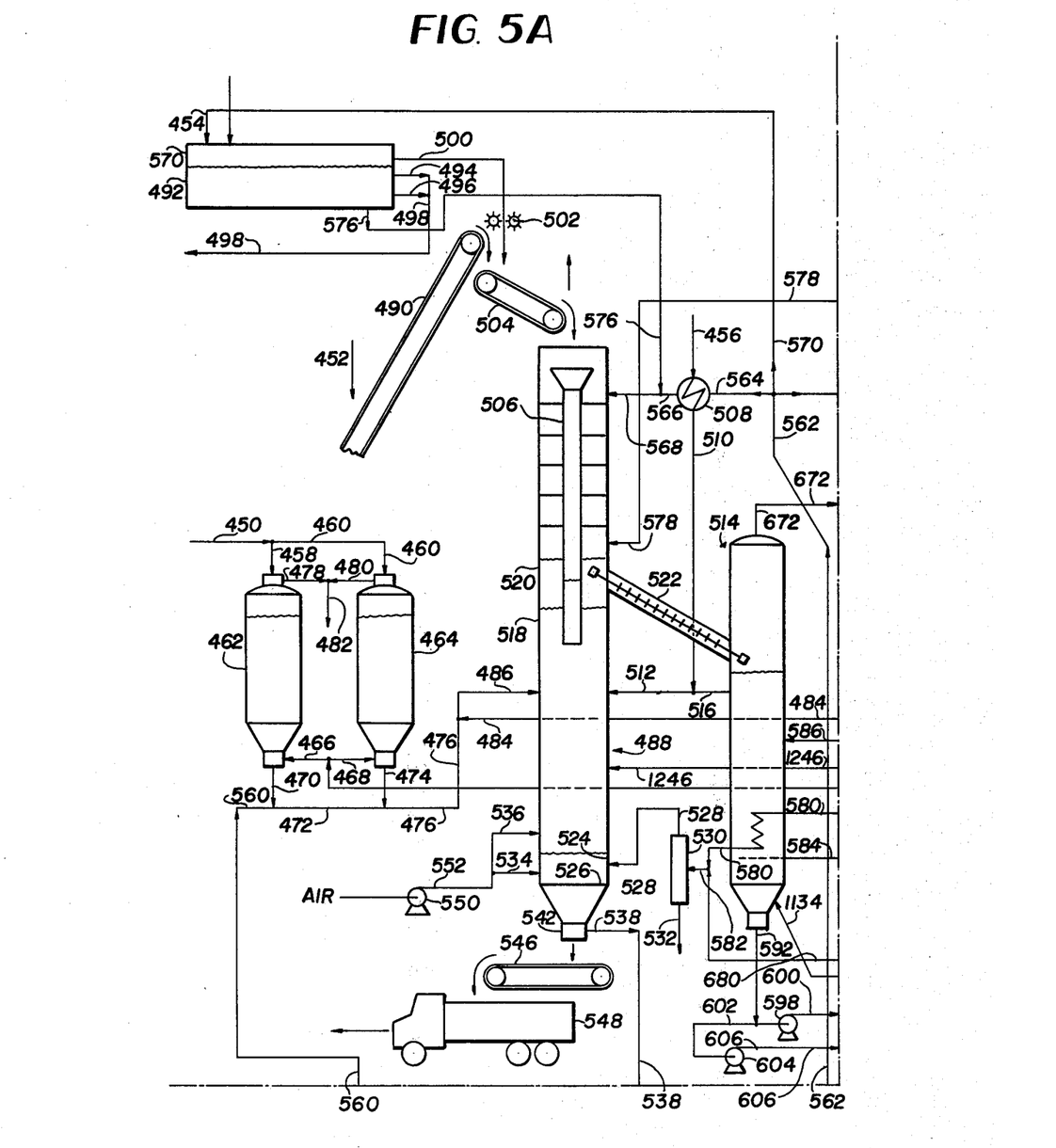
Figure 5B:
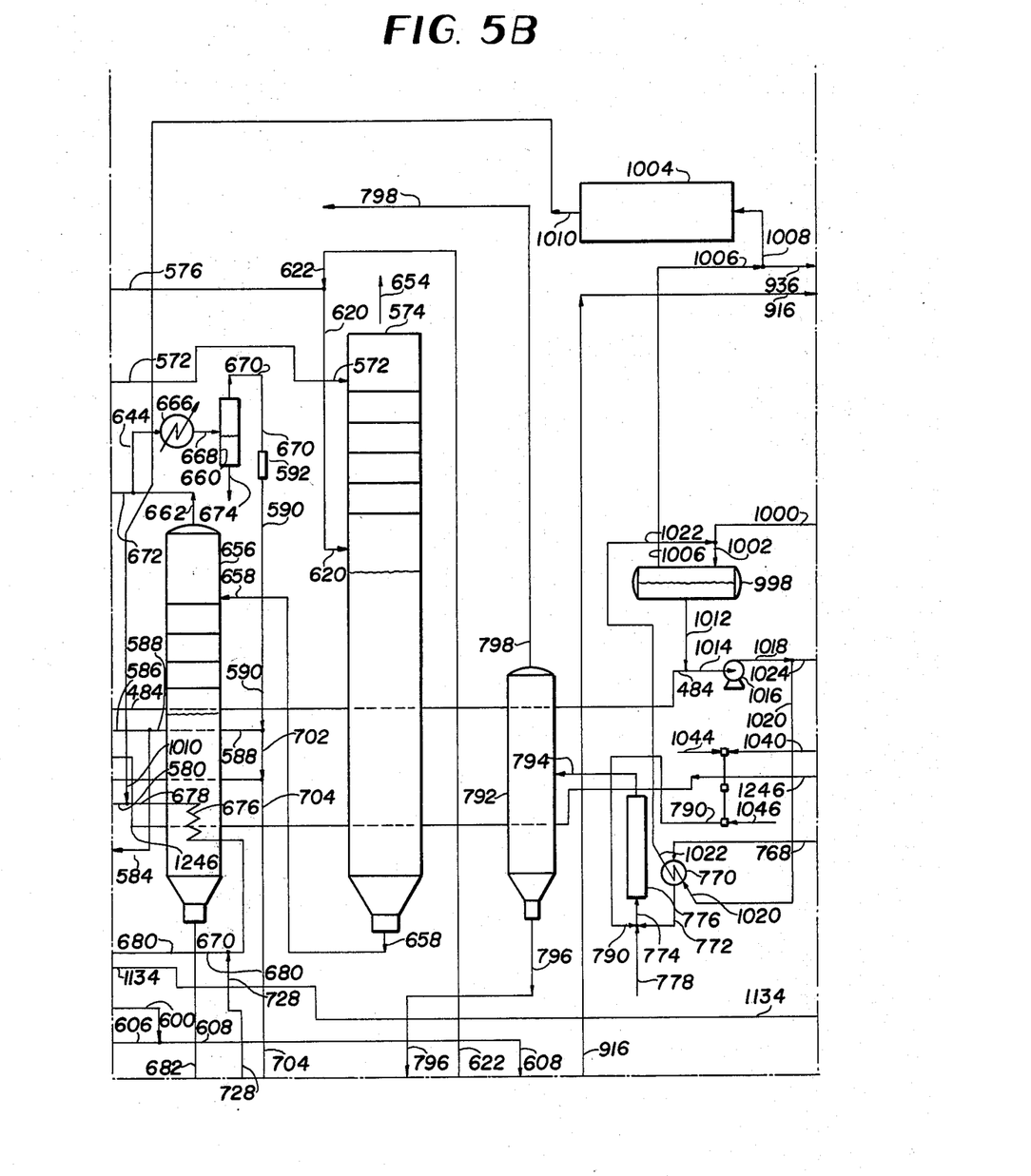
Figure 5C:
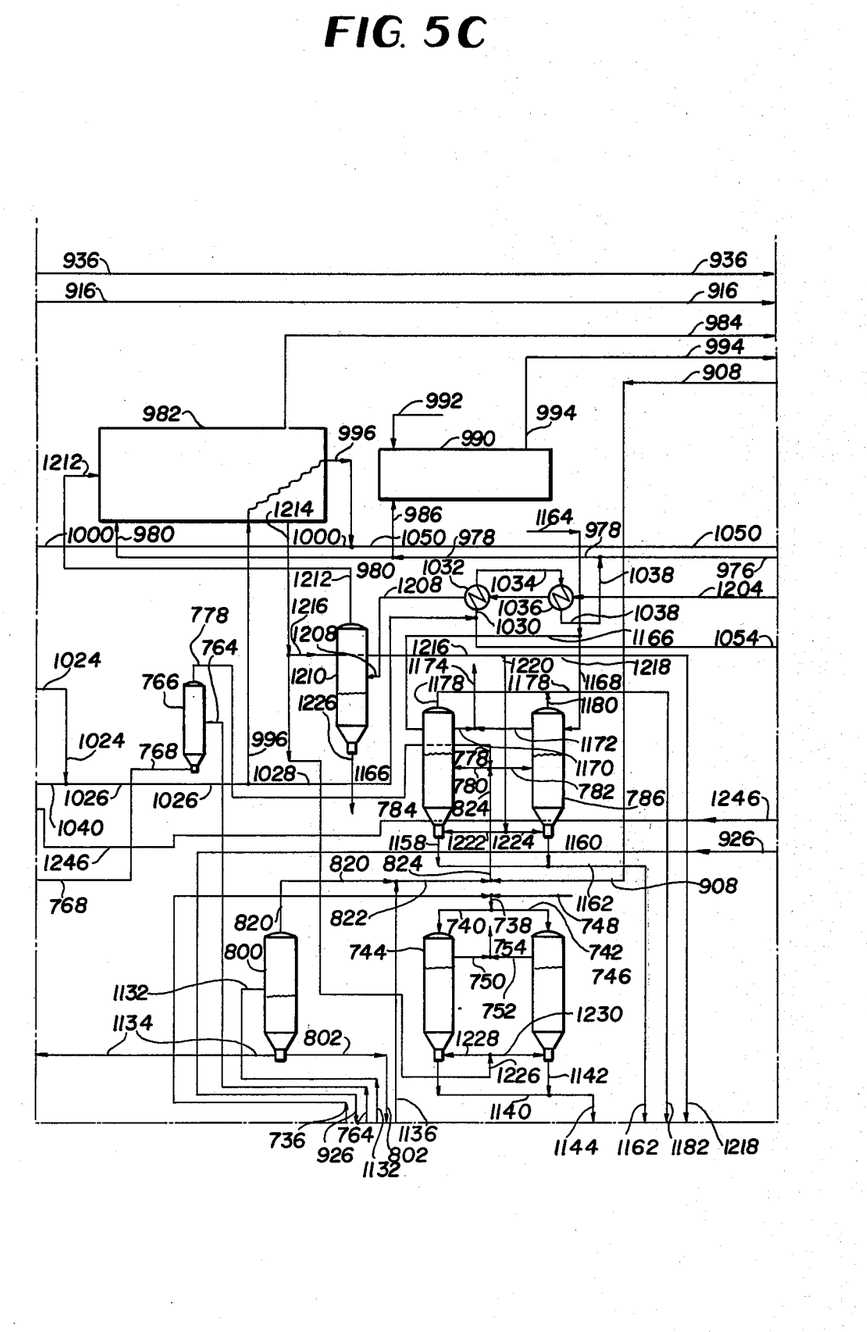
Figure 5D:
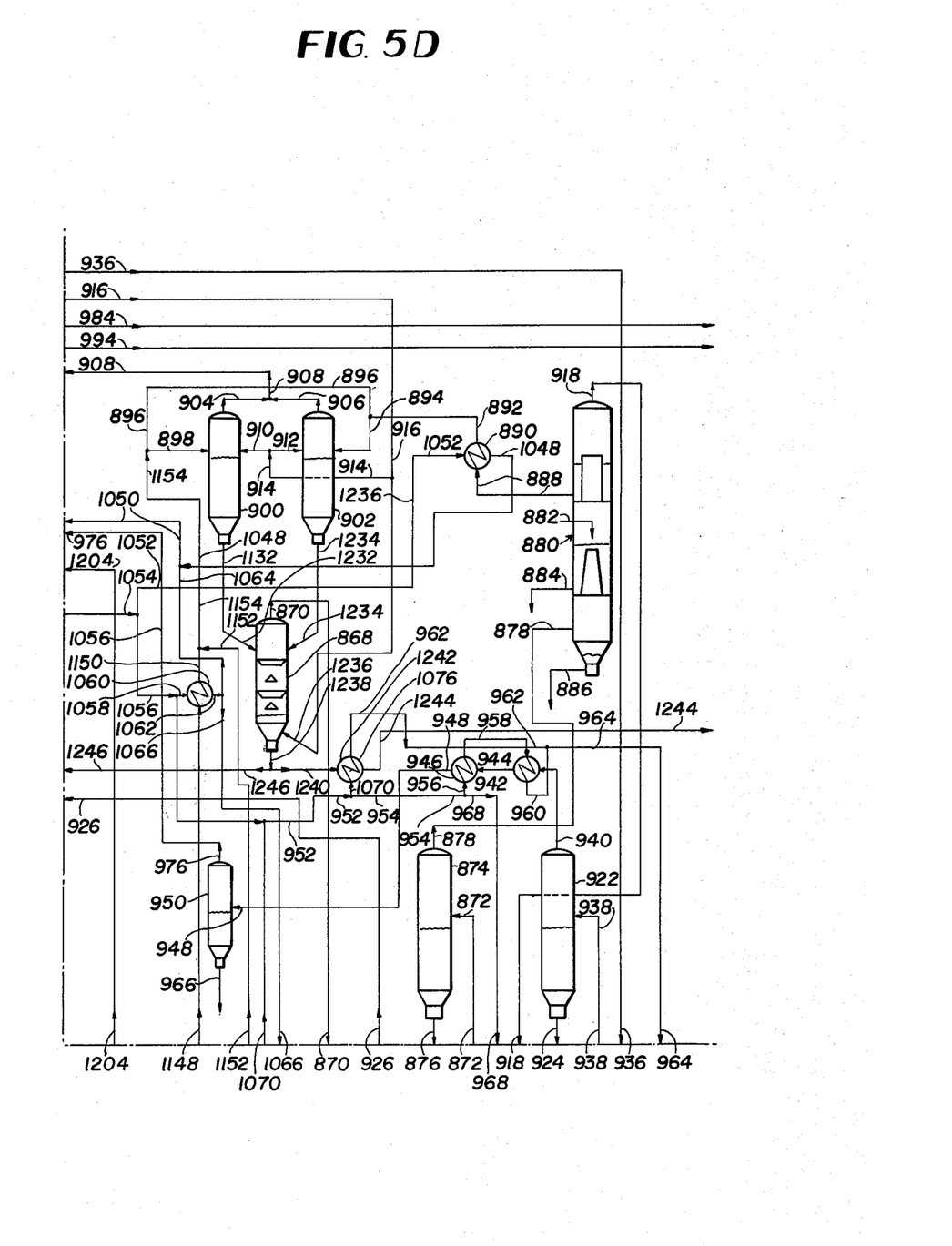
Figure 5E:
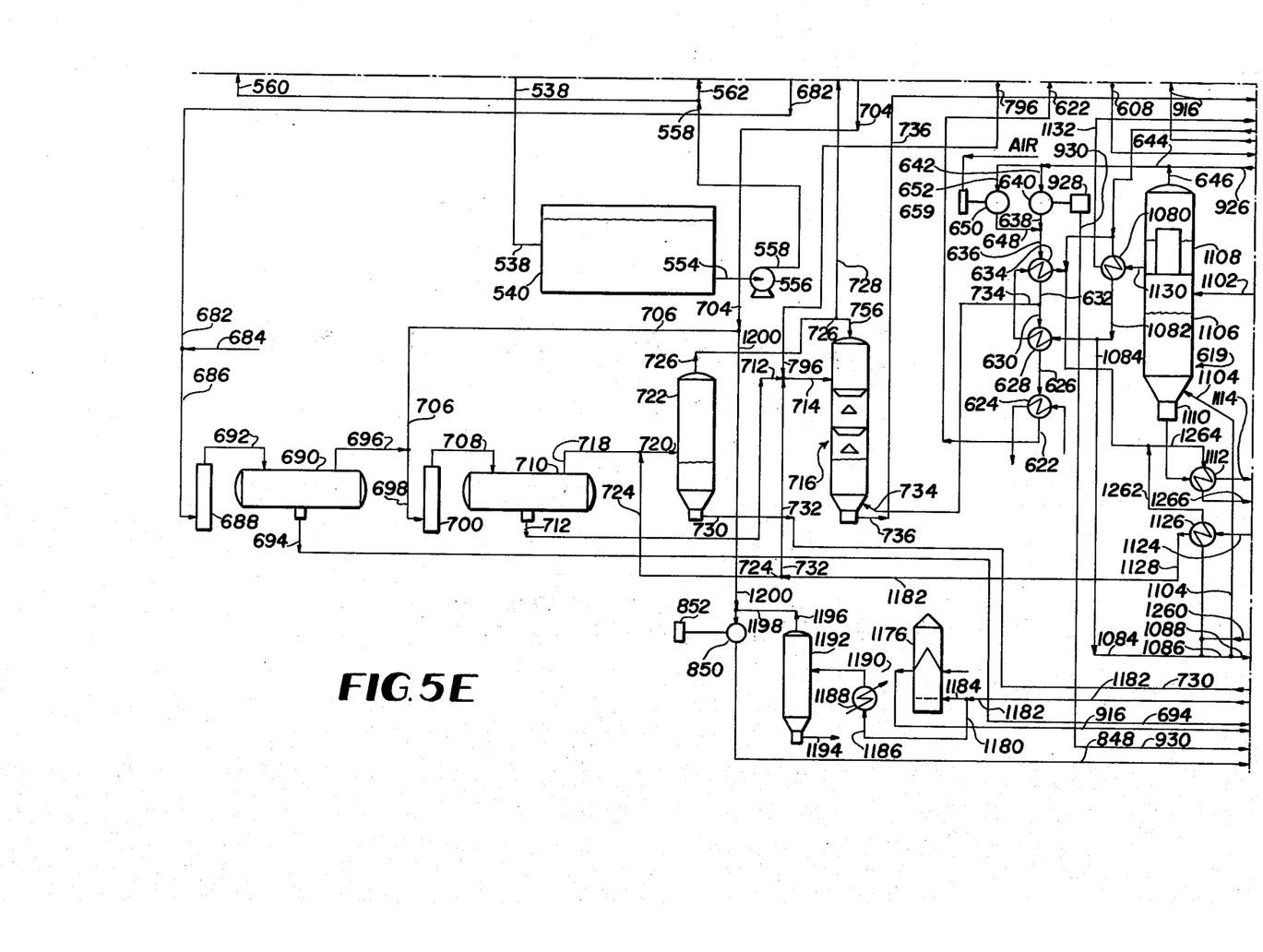
Figure 5F:
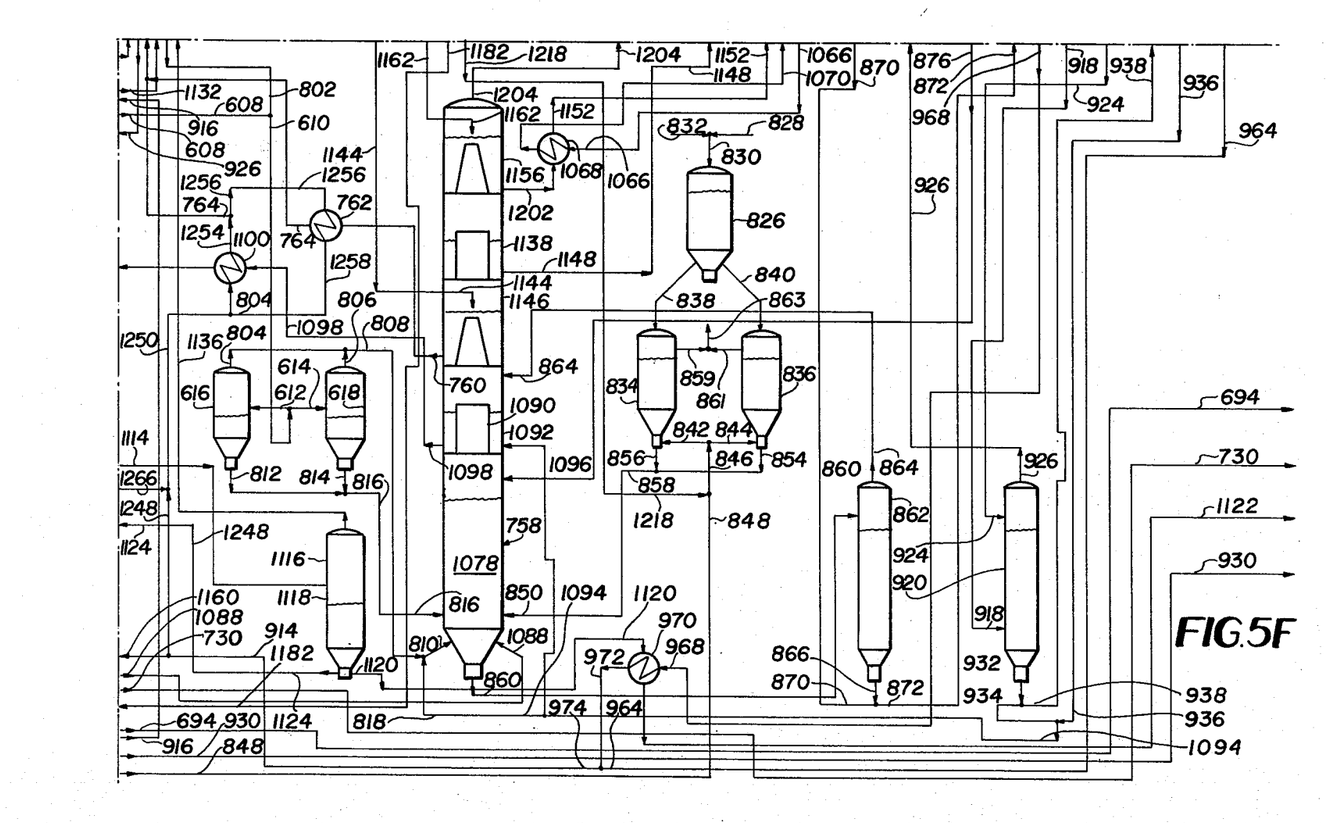

FIG. 4 is a schematic drawing of a multi-tray gasifier-treater reactor and a methanol converter reactor suitable for use with the subject invention.

Combustibles and steam are fed into the lowest tray, in which the gasification reaction takes place and the clay is circulated. Previously prepared dried solid waste is lock-binned into a bed of fluidized clay 350 in a bottom zone gasifier 352 via lines 354 and 356. Dried pulverized coal is lock-binned into the bed of fluidized clay 350 via line 356. Steam is injected into the bed of fluidized clay 350 via line 358 to accomplish the gasification. The carbonated clay is circulated via line 360 and mixed with hot air from line 362. The lines 360 and 362 join to form line 364, which leads to a vessel 366. The residual carbon is burned off the clay and the clay is separated from the exhaust gases in vessel 366. The hot clay is returned to the bottom zone gasifier 352 via line 368, and the exhaust gases exit the vessel 366 via line 370, after which they are used to drive a turbine and/or an electric generator (not shown). Powdered ash from the bottom zone gasifier 354 flows upwardly via a chimney 372 to the next higher process tray.

In the ash separating zone 374, the ash settles downward in an annular accumulator 376, after which it is pressured to storage via line 378. Meanwhile, the producer gases flow upwardly to the next higher process tray, contact tray 380.

In the limestone treating zone 382, limestone reagent ($CaCO_3$ and $BaCO_3$) is injected via line 384. Chlorine gas (which is a producer gas) from the ash separating zone 374 reacts with the $BaCO_3$ to yield $BaCl_2$, which gravitates to an annular bottom area 386, after which it is pressured out to storage via line 388. Sulfur gas (i.e., $H_2S$, which is also a producer gas) from the ash separating zone 374 reacts with the $CaCO_3$ to yield CaS, which floats upward to the next higher process tray via chimney 390 and then gravitates downward in an annular CaS accumulator 392, after which it flows via line 394 to an oxidizer 396. In the oxidizer 396, air from line 398 exothermically oxidizes the CaS to $CaSO_4$, which is then pressured to storage via line 400. Excess heated air flows via lines 362 and 364 to the vessel 366. Meanwhile, the remaining producer gases flow upwardly to the next higher process tray, contact tray 402.

In the high temperature precipitator zone 404, high temperature precipitator reagent is injected via line 406. The high temperature precipitator reagent can be blended as coarse Attapulgas clay (4 to 30 mesh) and $BaCO_3$ powder. Alternatively, some coarse coal ash from western U.S. coal contains coarse clay and $BaCO_3$ powder and can be used as the high temperature precipitator reagent without further blending. Metallic chlorides in the remaining producer gases are precipitated with the $BaCO_3$ (e.g., $BaCO_3 + FeCl_2 \rightarrow BaCl_2 + FeO + CO_2$), and alkali compounds in the remaining producer gases are precipitated with the coarse Attapulgas clay (e.g., $SiO_2 \cdot Al_2O_3 + Na_2O \rightarrow SiO_2 \cdot Al_2 \cdot Na_2O$). The precipitated compounds settle out in a coarse ash accumulator 408, after which they are pressured to storage via line 410.

After these sequential treatments, the remaining producer gases are hot (1500° F.), ultraclean CO and $H_2$. They are now cooled down by a water/steam heat exchanger 412, after which they are compressed and pressured via a conventional methanol converter unit 414 to produce methanol as the desired product. The methanol converter unit 414, shown in schematic form at the right-hand side of FIG. 4, comprises a first catalyst bed 416, a cooler zone 418 containing another water/steam heat exchanger 420, a second catalyst bed 422, and an alcohol fractionator 424. The methanol is taken off via line 426.

Overall System

Referring now to FIGS. 5A through 5F, the presently preferred embodiment of the overall system will be described in detail.

The charging stocks are represented by the arrows 450 (for agricultural solid wastes), 452 (for municipal solid wastes), 454 (for industrial and commercial solid wastes), and 456 (for sewage water solid concentrates). The agricultural solid wastes 450 are conveyed via lines 458 and 460 into pressure lock-bins 462 and 464. Carbon dioxide pressurizing gas from lines 466 and 468 pressures the chopped agricultural solid wastes 450 into the bottom nozzle of the lock-bins 462 and 464 and into the water circulating lines 470, 472, 474, and 476. Lines 478, 480, and 482 provide a vent for lock-bins 462 and 464. Hot boiler blowdown water from line 484 is added to preheat the chopped agricultural solid wastes 450 in line 486 and to convert them into a solid-water slurry. The slurry is then forced into an exhaust heat recovery stack 488.

The municipal solid wastes 452 are chopped sufficiently to travel upwardly on conveyor 490 prior to their deposit thereon.

The industrial and commercial solid wastes 454 are separated in a hot water preseparator basin 492. The nonbuoyant solids are discarded via lines 494, 496, and 498 to landfill or to a recycling operation. Buoyant solids are transported via line 500, through crusher 502, to conveyor 504, where they are joined with the chopped municipal solid wastes 452 from conveyor 490. The mixed chopped municipal solid wastes 452 and crushed buoyant industrial and commercial solid wastes 454 are then transported to the exhaust heat recovery stack 488 via downcomer 506.

The sewage water solid concentrates 456 are preheated in a heat exchanger 508 and are then pressured into the exhaust heat recovery stack 488 via lines 510 and 512 or into a water evaporator 514 via lines 510 and 516, depending upon the quality of the sewage water solids.

The combined solid wastes 450, 452, 454, and 456 are preheated, disintegrated, and separated in a bottom hot water zone 518 in the exhaust heat recovery stack 488. The organic combustible portion of the solid wastes 450, 452, 454, and 456 floats on top of the water bath into a zone 520. A grinding auger 522 forces these organic particles from the zone 520 into the water evaporator 514. Since the inorganic and polyvinyl chloride plastics portion of the solid wastes is, in general, non-buoyant, it sinks in the water to a bottom zone 524 bounded on the bottom by an aggregate filter 526. A small, controlled amount of calcium sulfate is injected into the bottom zone 524 via a line 1246. Air and carbon dioxide from exhaust gases also enter the exhaust heat recovery stack 488 via lines 534 and 536, making the solution just sufficiently acidic to dissolve the iron and aluminum cans from the municipal wastes 452 in bottom zone 524.

The aggregate filter 526 allows clear water to flow out a line 538 to a hot water surge tank 540. Dirt, glass, and polyvinyl chloride plastics collect on top of aggregate filter 526, and they are removed periodically via flange 542, conveyor 546, and truck 548. Because of the acidic-water environment in bottom zone 524, some heavy trace metals, such as lead, copper, bismuth, tin, and cadmium will precipitate, collect on the aggregate filter 526, and be discharged with the dirt, glass, and polyvinyl chloride plastics. To maintain good contact, air is injected along with the carbon dioxide by pump 550 into the bottom zone 524 via lines 552 and 534.

Hot water from surge tank 540 is pumped via line 554, pump 556, line 558, and line 560 to mix with chopped agricultural solids 452 from lock-bin 462 in the water circulating line 472. Additionally, hot water from surge tank 540 is pumped via line 554, pump 556, line 558, line 562, line 564, heat exchanger 508, line 566, and line 568 to exhaust heat recovery stack 488; via line 554, pump 556, line 558, line 562, and line 570 to hot water preseparator basin 492; and via line 554, pump 556, line 558, line 562, and line 572 to hot water removal tower 574. Hot water from the hot water preseparator basin 492 drains through lines 576 and 5568 to the exhaust heat recovery stack 488. Heat, water, and some carbon dioxide from exhaust gases enter the exhaust heat recovery stack 488 via line 578.

In the water evaporator 514 steam from line 580 indirectly supplies heat to drive water and carbon dioxide out of the evaporator. The steam then enters the water separator 530 via line 582. Some carbon dioxide is supplied to the water evaporator 514 via lines 584 and 586 to make better contact and to integrate the organic solids into a pumpable mud. The carbon dioxide enters the lines 584 and 586 via lines 588 and 590, the latter of which emanates from a carbon dioxide pump 592. The mud-slurry is pumped from water evaporator 514 via line 594, line 596, pump 598, line 600, and via line 592, line 602, pump 604, line 606, line 608, line 610, and lines 612 and 614 to steam generators 616 and 618, respectively.

In the hot water removal tower 574, the iron, aluminum, calcium, and barium salts are concentrated in water solution. Exhaust gases from an ash decarbonizer tower 619 (described hereinafter) enter hot water removal tower 574 via lines 620 and 622, heat exchanger 624, line 626, heat exchanger 628, line 630, line 632, heat exchanger 634, line 636, and, alternatively, line 638, gas expander 640, line 642, line 644, and line 646 or line 648, gas expander 650, line 652, line 644, and line 646. The exhaust gases drive steam, carbon dioxide, and nitrogen out of the hot water removal tower 574 via duct 654. Hot water from the hot water removal tower 574 drains to a carbon dioxide removal tower 656 via line 658. An air compressor 659 is operatively connected to the gas expander 650.

Carbon-dioxide is forced from the carbon dioxide removal tower 656 to a water separator stripper 660 via line 662, line 664, heat exchanger 666, and line 668. Carbon dioxide pump 592 pulls the carbon dioxide out of the water separator stripper 660 via line 670. The carbon dioxide pump 592 also pulls the carbon dioxide out of the water evaporator 514 via line 672, line 644, heat exchanger 666, line 668, water separator stripper 660, and line 670. The water separator stripper 660 is drained via line 674. Steam passed through a heat exchanger 676 in line 678 helps strip carbon dioxide from the carbon dioxide removal tower 656. The steam then passes through line 580 and line 582 to water separator 530.

The diverted and concentrated metallic salts are pumped from the carbon dioxide removal tower 656 via line 682 to a metallic fractionating and recovery system. Process ammonia from a feed 684 is contacted with the soluble concentrated metallic salts in a line 686 leading to a contact mixer 688 to precipitate the iron, aluminum, and other heavy trace metals (Hg, Ni, Co, Mn, Zn, and Cr). The mixture is passed from the contact mixer 688 to a horizontal separator 690 via a line 692. The horizontal separator 690 allows the precipitates to settle to the bottom, from which they may be pressured out to storage via line 694 as a water slurry composed primarily of iron and aluminum hydroxide. The slurry may be sold as a pumpable chemical feedstock.

Following the removal of the heavy metals, the clear water from the horizontal separator 690 is drawn via line 696 and line 698 to a contact mixer 700 by carbon dioxide pumped by the carbon dioxide pump 592 via line 590, line 702, line 704, line 706, and line 698. From the contact mixer 700, the clear water is passed via line 708 to horizontal settling tank 710. The calcium and barium carbonates in the water are precipitated and allowed to settle to the bottom of the horizontal settling tank 710. The settled calcium and barium carbonates are then pressured via line 712 and line 714 to a drier tower 716. The clean water in horizontal settling tank 710 contains soluble ammonium bisulfate, and this clear water is pressured via line 718 and line 720 to a concentrator tower 722. To help remove water, some hot ash is injected into the concentrator tower 722 via line 724 and line 720. The evaporated water exits the concentrator tower 722 via line 726, whence it passes through line 728 to line 680. The concentrated ammonium sulfate in water solution in concentrator tower 722 goes to storage with the solid ash via line 730. Since the ash is an absorbing material, traces of herbicide (furfural), some potash ($K_2O$), and some phosphate ($P_2O_5$) may be entrained with this mixed nitrogen fertilizer water slurry. Because the coarse ash powder is quite stable, it may function as a soil conditioner for beneficial agricultural uses when evenly distributed on cultivated land.

Line 732 carries hot ash to the drier tower 716 via line 714, where the hot ash provides heat to help evaporate water from the slurry of calcium and barium carbonates. However, most of the water in the drier tower 716 is removed by injecting warm exhaust gases from the heat exchanger 634 into the drier tower 716 via line 632 and line 734. The largest portion of the barium and calcium carbonates is recovered from the drier tower 716 via line 736. The dried calcium and barium carbonates are pressured as recycle limestone via line 736, line 738, and lines 740 and 742 to lock-bins 744 and 746, respectively. Make-up limestone is injected into the lock-bins 744 and 746 via line 748, line 738, and lines 740 and 742, respectively. As the make-up limestone is injected into the lock-bins 744 and 746, displaced air is vented via lines 750, 752, and 754. Steam is recovered from the drier tower 716 via line 756, which joins the line 726 to form line 728.

The primary barium chloride regeneration phase is handled separately because it is essential to remove the chlorine from the plant as soon as possible. Spent barium chloride from a coal reactor 758 is fed via line 760, heat exchanger 762, line 764, contactor 766, line 768, heat exchanger 770, line 772, and line 774 to contactor column 776. Exhaust gases from the contactor 766 pass via line 778 and lines 780 and 782 to the lock-bins 784 and 786, respectively.

Sodium carbonate is also fed into contactor column 776 via lines 778 and 774, and water is fed into contactor column 776 via lines 790 and 774. The barium chloride is converted to barium carbonate, transferred to tower 792 via line 794, and settled as a precipitate in tower 792. The barium carbonate is then pressured to the drier tower 716 via lines 796 and 714. The by-product sodium chloride produced in the contactor column 776 is soluble in water, and can therefore be pressured overhead from the tower 792 via line 798 to a solar evaporation pond (not shown).

Hot fine ash from a depressuring tower 800 is transferred to the steam generators 616 and 618 via lines 802, 610, and lines 612 and 614, respectively. In the steam generators 616 and 618 it mixes with the organic solid-water slurry to dry the organic solids. The dirty steam from the steam generators 616 and 618 is transferred via lines 804, 806, 808, and 810 to the bottom of the coal reactor 758. Similarly, the dried organic solid powder from the steam generators 616 and 618 is pressured via lines 812, 814, and 816 to the coal reactor 758. Additional steam is supplied to the line 810 via line 818. Waste gases from the depressuring tower 800 pass through lines 820, 822, 824 and lines 780 and 782, respectively, to lock-bins 784 and 786.

Raw pulverized coal is fed into a coal hopper 826 from lines 828 and 830, and fine Attapulgus clay and/or barium carbonate anti-caking additive (0.1% wt.) is fed into the coal hopper 826 from lines 832 and 830. The additive and the coal are then fed into coal lock-bins 834 and 836 via lines 838 and 840, respectively. Pressurizing gas is fed into the lock-bins 834 and 836 via lines 842, 844, 846, and 848 by carbon dioxide compressor 850 powered by motor 852 in order to force the coal to auger feeds 854, 856, and 858, which control the rate of coal fed to the coal reactor 758. Exhaust gases are vented from the lock-bins 834 and 836 via lines 859, 861, and 863.

To provide processing heat, hot clay is fed from the bottom of the coal reactor 758 (where it is at approximately 1000° F.) via a line 860 to a clay surge tank 862. Exhaust gases from the clay surge tank 862 are returned to the coal reactor 758 via line 864. The clay leaves the bottom of the surge tank 862 via line 866. Exhaust gases and air from an oxidizer chamber 868 (described hereinafter) are conducted via line 870, which joins line 866 to form a riser pipe 872 in which the residual carbon is burned off the clay to produce both carbon monoxide and carbon dioxide. The riser pipe 872 leads to a separator tank 874 in which the clay settles to the bottom. The clay is then recycled from the separator tank 874 back to the coal reactor 758 via line 876 at about 1000° F.

The producer gases (carbon monoxide, carbon dioxide, and nitrogen) from the separator tank 874 are pressured via line 878 to a limestone treater 880. Limestone is fed into the limestone treater 880 via line 882 to convert the residual hydrogen sulfide in the limestone treater 880 to calcium sulfide. Vents 884 and 886 are provided for waste products. The calcium sulfide is then discharged from the limestone treater 880 via line 888, heat exchanger 890, and lines 892, 894, 896, and 898 to lock-bins 900 and 902. Exhaust gases from the lock-bins 900 and 902 exit via lines 904, 906, 908, 824, 780, and 782, the latter leading to the lock-bins 784 and 786, respectively. Process air is fed into the lock-bins 900 and 902 via lines 910, 912, 914, and 916.

The treated producer gases leave the limestone treater 880 through line 918 which leads to a metal reducing tower 920. In the metal reducing tower 920 the carbon monoxide fuel gas is completely burned by circulating hot metal oxide (stainless steel) powder which enters the metal reducing tower 920 from a separator tank 922 through line 924. The burned fuel gas exits the metal reducing tower 920 via line 926, line 644, and lines 642 and 652 to help drive gas expanders 640 and 650, respectively. The gas expander 640 in turn drives electrical generator 928, which provides a salable output of electrical power represented by the line 930.

The reduced metal reagent leaves the bottom of metal reducing tower 920 via line 932. Steam from lines 934 and 936 lifts the reduced metal reagent from line 932 upwardly through riser pipe 938 in which the reduced metal reagent is oxidized and hydrogen gas is generated. The riser pipe 938 leads to separator tank 922 in which the oxidized metal reagent settles to the bottom. The oxidized metal reagent in separator tank 922 is then recycled to the metal reducing tower 920 via line 924, as previously mentioned. When ammonia production is required, nitrogen is included with the hydrogen production by injecting a small amount of air into the separator tank 922 by means not shown.

The hydrogen gas produced in the riser pipe 938 is pressured from the separator tank 922 via line 940, heat exchanger 942, line 944, heat exchanger 946, and line 948 to a water separator 950. Steam is supplied to the heat exchangers 946 and 942 via lines 952, 954, 956, and 958, after which the steam exits heat exchanger 942 via line 960, which joins line 962 to form line 964. Waste water exits the water separator 950 via line 966. Water from line 954 additionally passes through line 968, heat exchanger 970, and line 972, which joins line 964 to from line 974. The hydrogen is then fed from the water separator 950 via lines 976, 978, and 980 to a methyl alcohol converter unit 982. Methyl alcohol is withdrawn from the methyl alcohol converter unit 982 via line 984, and it may be sold as such.

If combined hydrogen and nitrogen are produced in the separator tank 922, the gas mixture is fed from the water separator 950 via lines 976, 978, and 986 to an ammonia converter unit 990. Additional nitrogen may be added to the ammonia converter unit 990 via the line 992. Ammonia is withdrawn from the ammonia converter unit 990, via line 994, and it may be sold as much.

The methyl alcohol converter unit 982 also acts as a heat exchanger. Line 996, which passes through methyl alcohol converter unit 982, contains water when it enters the unit and steam when it exits it. From the methyl alcohol converter unit 982, the steam goes to a steam chest 998 via lines 996, 1000, and 1002. Steam from the steam chest 998 goes to an exhaust steam unit 1004 via lines 1006 and 1008, and steam from the exhaust steam unit 1004 goes to the carbon dioxide removal tower 656 via lines 1010 and 678. Water from the steam chest 998 goes through lines 1012, 484, and 486 to the exhaust heat recovery stack 488; through lines 1012 and 1014, a pump 1016, lines 1018 and 1020, the heat exchanger 770 (where it is changed back to steam), and lines 1022 and 1002 back to the steam chest 998; and through lines 1012 and 1014, the pump 1016, lines 1018, 1024, 1026, and 996 to the methyl alcohol converter unit 982.

Water from the line 1026 additionally passes through the line 1028, line 1030, heat exchanger 1032, line 1034, heat exchanger 1036, and line 1038 to join line 976 to form line 978. Also, water from the line 1024 passes through lines 1040, 1042, 790, and 774 to enter the contactor column 776. Make-up water is supplied to line 1040 via line 1044 and to line 1042 via line 1046.

Steam from heat exchanger 890 passes through lines 1048 and 1050 to join line 996 to form line 1000. Water is supplied to the heat exchanger 890 from the steam chest 998 via lines 1052, 1054, 1028, 1026, 1024, 1018, pump 1016, and lines 1014 and 1012. Water from the line 1054 is also passed through lines 1056 and 1058, heat exchanger 1060, lines 1062, 1064, 1050, 1000, and 1002 to the steam chest 998, while steam from line 1062 passes through line 1066, heat exchanger 1068, line 1070, line 952, and line 1074 to heat exchanger 1076.

Now returning to the coal reactor 758, the hot fluidized clay at about 1600° F. in zone 1078 and steam injected from line 810 gasify the organic solids and coal to primarily carbon monoxide and hydrogen ($C+H_2O \rightarrow H_2+CO$). On plant start-up, hot air from heat exchanger 1080 is injected into the hot fluidized clay in zone 1078 via lines 1082, 1084, 1086, and 1088 to help to fluidize the bed. The ash powder and producer gas flow up through a first chimney 1090, after which the ash settles in an annular ash accumulator 1092. Steam from line 936 transmitted via lines 1094 and 1096 removes more carbon from the ash, after which the ash exits through a line 1098, a heat exchanger 1100, and a line 1102 to the ash decarbonizer tower 619. Air entering the ash decarbonizing tower 619 from the air compressor 659, and burns nearly all the carbon off the ash, but also separates the ash into a coarse fraction 1106 and a fine fraction 1108. The coarse fraction 1106 flows out the bottom of ash decarbonizer tower 619 via line 1110, steam generator 1112, and line 1114 to a depressuring tower 1116. The coarse ash is accumulated in a bottom zone 1118 of the depressuring tower 1116, after which it goes to product storage via a line 1120, heat exchanger 970, and a line 1122 and/or to recycle via a line 1124, a heat exchanger 1126, line 1128, line 732, and line 714 or via line 1124, heat exchanger 1126, line 1128, line 724, and line 720. The fine fraction 1108 from the ash decarbonizer tower 619 flows via a line 1130, heat exchanger 1080, and a line 1132 to the depressuring tower 800. The fine hot ash from the depressuring tower 800 is distributed two ways: via lines 802, 610, 612, and 614 to steam generators 616 and 618 and also via line 1134 to the water evaporator 514. Exhaust gases from the depressuring tower 1116 pass through lines 1136, 822, 824, 780, and 782 to enter lock-bins 784 and 786.

Limestone or calcium carbonate is used in the coal reactor 758 to remove hydrogen sulfide as calcium sulfide in zone 1138. Barium carbonate from the lock-bins 744 and 746 is injected via line 1140, 1142, and 1144 to remove hydrogen chloride as barium chloride in zone 1146. Since barium carbonate and barium chloride are substantially heavier than the corresponding calcium salts, the barium salts stay in the zone 1146. Also, since barium chloride has a much higher fusion point than calcium carbonate, the barium used for chlorine removal removes much more chlorine than calcium. Calcium sulfide exits zone 1138 via line 1148, heat exchanger 1060, and line 1150, which joins line 1152 to form line 1154.

The producer gas in the coal ractor 758 is finally purified by injecting a high temperature precipitator (HTP) into treating zone 1156 from lock-bins 784 and 786 via lines 1158, 1160, and 1162 to remove submicronic particles and residual vaporous metal halides from the producer gas. The HTP is supplied to the lock-bins 784 and 786 via lines 1164, 1166, and 1168. Waste gases are vented from the lock-bins 784 and 786 via lines 1170, 1172, and 1174. Fuel gas is fed from the lock-bins 784 and 786 to a start-up heater 1176 via lines 1178, 1180, 1182, and 1184. Additionally, carbon dioxide is fed from the line 1182 through line 1186, heat exchanger 1188, and line 1190 to carbon dioxide cleaning drum 1192. Impurities culled from the carbon dioxide cleaning drum 1192 are discarded via line 1194, and clean carbon dioxide is supplied to the carbon dioxide recycle compressor 850 via lines 1196 and 1198. Additional carbon dioxide is supplied to the carbon dioxide recycle compressor 850 via lines 704, 1200, and 1198.

In the present invention, barium carbonate is one constitutent of the HTP, It is present to remove the organic halides (i.e., barium chloride and barium fluoride). The other principal constituent of the HTP is coarse Attapulgas clay (15 to 30 mesh). It is present to chemically combine such alkali metals as potassium and sodium to produce spinal and to precipitate the submicronic particulates. The spent HTP is removed from treating zone 1156 via line 1202, heat exchanger 1068, line 1152, line 1154, and line 898 to the lock-bin 900 or to a separate disposal system.

The clean producer gas exits the coal reactor 758 via a line 1204, heat exchanger 1036, line 1206, heat exchanger 1032, and line 1208 leading to a water separator 1210. The producer gas then exits the water separator 1210 via a line 1212 leading to the methyl alcohol converter unit 982. To balance the hydrogen and carbon monoxide ratio in the methyl alcohol converter unit 982, the vent gases from the methyl alcohol converter unit 982 are recycled via lines 1214, 1216, 1218, 846, 842, and 844 to the coal lock-bins 834 and 836 and via lines 1214, 1216, 1220, 1222, and 1224 to the lock-bins 784 and 786. Wastes from the water separator 1210 are discarded via drain line 1226. Additionally, vent gases from the methyl alcohol converter unit 982 pass through the lines 1214, 1226, 1228, and 1230 to the lock-bins 744 and 746.

Calcium sulfide from the lock-bins 900 and 902 is supplied to the oxidizer chamber 868 via lines 1232 and 1234, respectively. To oxidize the calcium sulfide to calcium sulfate, process air is fed from the start-up heater 1176 into the oxidizer chamber 868 via lines 916 and 1236. The calcium sulfate in the oxidize chamber 868 is pressured to storage via lines 1238 and 1240, heat exchanger 1242, and line 1244. Some of the calcium sulfate from the oxidizer chamber 868 is charged via lines 1238 and 1246 to the bottom zone 524 of the exhaust heat recovery stack 488, where it facilitates iron and aluminum solution, after which it is reprecipitated in horizontal separator 690, as previously explained. The operating flexibility is sufficient to vary the ratio of feed stocks and the product over a broad range.

Steam from the heat exchanger 1076 passes through lines 962, 964, and 974. From line 974, some of the steam passes through lines 1248, 1250, and 1252 to heat exchanger 1100, line 1254, line 1256, heat exchanger 762, and line 1258 back to line 1252. Another fraction of the steam from line 974 passes through line 1260, heat exchanger 1126, line 1262, line 1264, heat exchange 1112, and line 1266 to rejoin line 1248 to from line 1250.

Since the widely varying qualities and quantities of the various feed stocks are unpredictable, the quality and quantity of the process additives and reagents have to be adjusted as required to accomplish the optimum plant performance. Generally speaking, the following process additives are injected as required to serve their individual purposes:

(1) in the hot water circulating system, the temperature is controlled to absorb sufficient carbon dioxide to control the acidity in the bottom zone 524 of the exhaust heat recovery stack 488 so as to dissolve the metal (mostly iron and aluminum from the municipal wastes) as the calcium sulfate additive is injected.

(2) In the horizontal separator 690, ammonia is injected to alkalize the concentrated water solution to precipitate the iron and aluminum as hydroxides.

(3) In the horizontal settling tank 710, carbon dioxide as injected to precipitate the calcium and barium as carbonates.

(4) In concentrator tower 722, the ammonium sulfate is concentrated further by water evaporation.

(5) Barium carbonate is the more common additive because chlorine is a very serious trouble maker whenever hydrogen chloride is generated. Therefore, barium carbonate is used sparingly wherever it is required.

(6) The fine clay additive is used to spinal the potassium and sodium extrusions so as to carry these combined powdered solids into the ash by-products.

(7) The coarse clay reagent is used to rapidly distribute heat evenly, to carry clean carbon deposits to the external air burner, and to fluidize out the ash to the next upper zone.

(8) The dry limestone (calcium carbonate) is used primarily to remove hydrogen sulfide. The calcium sulfide by-product is air oxidized to the more valuable calcium sulfate. Some of the calcium sulfate is used to recover iron and aluminum, which are still more valuable by-products. In that process, the calcium sulfate is regenerated to calcium carbonate, and the sulfur is released as ammonium sulfate for fertilizer or chemical usage.

(9) The HTP is varied depending upon the nature of the contaminants to be removed:
  (a) For vaporous metallic holides, barium carbonate is used to precipitate the chlorine as barium chloride and the metal as solid salts.
  (b) For submicronic particulates, coarse Attapulgas clay is used to spinal the sodium and potassium compounds, which are then gravity separated from the producer gas.
  (c) Because coarsely powdered ash from high fusion coal ash (such as from several U.S. Western coals) contains natural HTP additives, such additives are used as HTP agents.

(10) Metal coating may be deposited on the 30-60 mesh clay fluidizing reagent to improve process performance. Such metals include tungsten, iron, cobalt, nickel, and chromium.

(11) To remove other metals in appropriate separating zones, hydrogen chloride or hydrogen sulfide is added to precipitate such metals from the circulating water solution.

While the present invention has been illustrated by a detailed description of a preferred embodiment thereof, it wil be obvious to those skilled in the art that various changes in form and detail can be made therein without departing from the true scope of the invention. For that reason, the invention must be measured by the claims appended hereto and not by the foregoing preferred embodiment.

I claim:
1. A process for coal and organic solid waste gasification comprising the steps of:
  converting water in an aqueous feed stock to steam;
  gasifying coal and organic solid waste feedstocks in the presence of said steam using a granular fluidized clay to produce a gaseous product composed primarily of carbon monoxide and hydrogen;
  removing hydrogen chloride from said gaseous product by injecting barium carbonate to react with hydrogen chloride to form barium chloride, and removing said barium chloride;
  removing hydrogen sulfide from said gaseous product by contacting said gaseous product with lime to react with hydrogen sulfide to from calcium sulfide, and removing said calcium sulfide for external oxidation to calcium sulfate and recovering said calcium sulfate;
  thereafter removing residual micronic particulates and vaporized metallic chlorides from said gaseous product using high temperature precipitating agents to finally clean the product gases consisting essentially of carbon monoxide and hydrogen;
  regenerating barium carbonate by reacting said recovered barium chloride with a water solution of sodium carbonate to from barium carbonate and sodium chloride;
  circulating carbon containing granular fluidized clay, used to gasify the coal and organic solid waste feedstocks in the presence of steam, to an air burner to burn said carbon to yield a producer gas containing carbon monoxide and carbon dioxide, and returning the decarbonized granular fluidized clay to gasify additional coal and organic solid waste feedstocks in the presence of steam; and
  reducing a metal oxide with said carbon monoxide in said producer gas to produce a reduced metal, and reoxidizing said reduced metal to metal oxide with steam to generate hydrogen gas.

2. The process set forth in claim 1, wherein said vaporized metallic chlorides removed using high temperature precipitating agents include iron chlorides.

3. The process set forth in claim 1, wherein said high temperature precipitating agents comprise coarse Attapulgas clay (4 to 30 mesh) and barium carbonate powder.

4. The process set forth in claim 1, wherein said coal and organic solid feedstocks are gasified in the presence of steam using a hot graunular fluidized clay of about 1700° F.

5. The process set forth in claim 1, including cooling, compressing and reacting said product producer gases consisting essentially of carbon monoxide and hydrogen to form methanol.

6. The process set forth in claim 1, wherein said organic solid waste feedstock includes any of agricultural solid waste, municpal solid waste, industrail and commercial solid waste, or sewage water solid concentrate.

7. The process set forth in claim 6, wherein said organic solid feedstock includes agricultural solid waste.

8. The process set forth in claim 6, wherein said organic solid feedstock includes municipal solid waste.

9. The process set forth in claim 6, wherein said organic solid feedstock includes industrial and commrcial solid waste.

10. The process set forth in claim 6, wherein said organic solid feedstock includes sewage water solid concentrate.

* * * * *